United States Patent [19]

Sorenson

[11] 4,454,764

[45] Jun. 19, 1984

[54] ROLLER-BALL ULTRASONIC IMAGING MODULE

[75] Inventor: Paul D. Sorenson, Blaine, Minn.

[73] Assignee: Medtronic, Inc., Minneapolis, Minn.

[21] Appl. No.: 414,703

[22] Filed: Sep. 3, 1982

[51] Int. Cl.$^3$ ............................................. G01N 29/00
[52] U.S. Cl. ........................................ 73/642; 73/644; 310/336
[58] Field of Search ................. 73/644, 642; 310/336; 128/660

[56] References Cited

U.S. PATENT DOCUMENTS

| | | | |
|---|---|---|---|
| 2,724,783 | 11/1955 | Renaut | 310/336 |
| 3,485,088 | 12/1969 | O'Connor | 73/644 |
| 3,952,582 | 4/1976 | Graham et al. | 73/644 |
| 4,097,835 | 6/1978 | Green | 73/642 |
| 4,242,912 | 1/1981 | Burckhardt et al. | 73/626 |
| 4,245,250 | 1/1981 | Tiemann | 358/140 |
| 4,246,791 | 1/1981 | Glenn | 73/620 |
| 4,252,026 | 2/1981 | Robinson | 73/626 |
| 4,253,338 | 3/1981 | Iinuma et al. | 73/626 |
| 4,265,121 | 5/1981 | Cribbs | 73/607 |
| 4,271,706 | 6/1981 | Ledley | 73/614 |
| 4,271,842 | 6/1981 | Specht et al. | 128/661 |
| 4,272,991 | 6/1981 | Cribbs | 73/621 |
| 4,297,886 | 11/1981 | Anikeev et al. | 73/642 |

FOREIGN PATENT DOCUMENTS 2036321  6/1980  United Kingdom .................. 73/644

*Primary Examiner*—Howard A. Birmiel
*Attorney, Agent, or Firm*—Robert J. Klepinski; John L. Rooney; Joseph F. Breimayer

[57] ABSTRACT

An ultrasonic imaging module including a housing having an internal fluid-filled chamber, and an ultrasonic transducer producing a beam of ultrasonic energy. The transducer includes a piezoelectric transducer element and a ball-shaped ultrasonic window rotatably mounted in a bearing in one wall of the chamber for transmitting the beam of ultrasonic energy to the object to be ultrasonically scanned while rolling on the object. A source of pressured fluid is connected to the chamber and the relative size of the bearing and roller-ball window are such that a film of ultrasonic coupling fluid is applied from the chamber to the surface of the object to be scanned as the roller-ball window turns in the bearing during the scanning process. An ultrasonic lens mounted in the chamber between the transducer element and the ball-window compensates for the effect of the sphericity of the window on the ultrasonic beam.

5 Claims, 3 Drawing Figures

U.S. Patent  Jun. 19, 1984  4,454,764
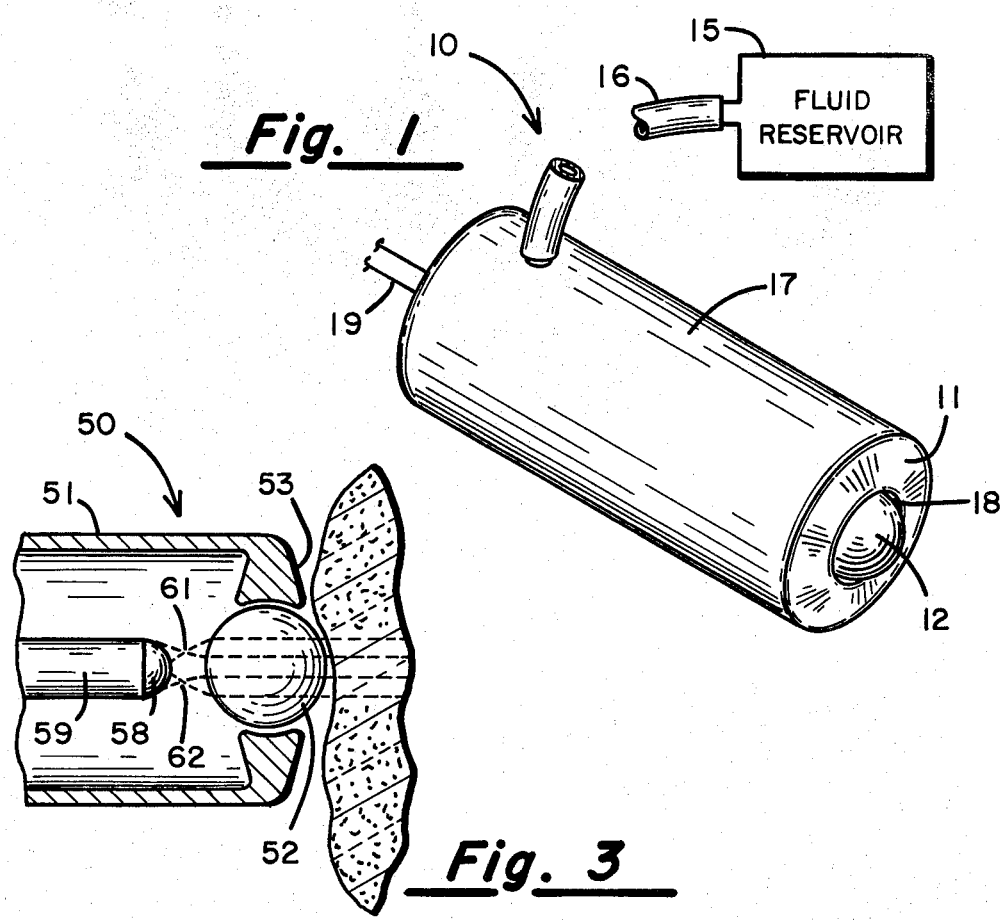
Fig. 1
Fig. 3
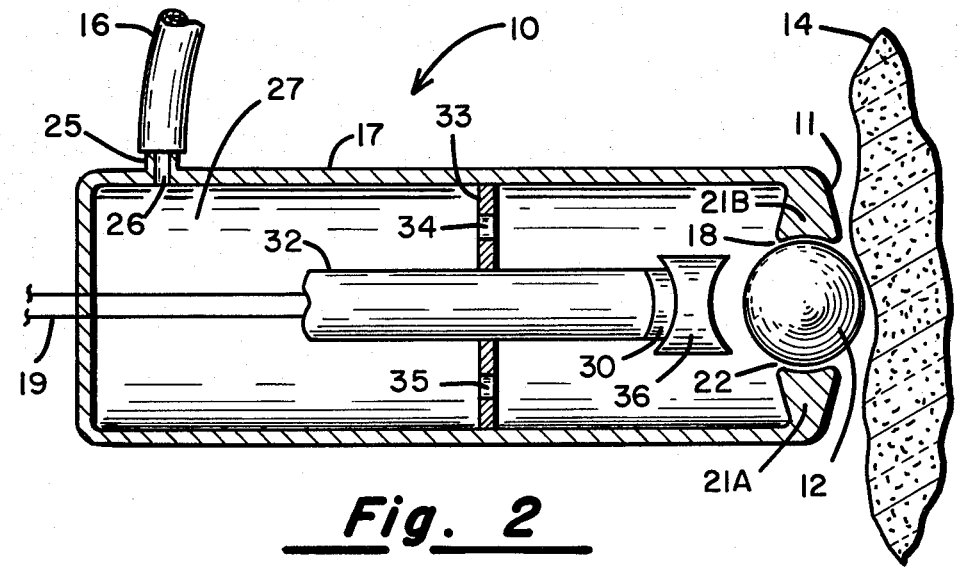
Fig. 2

ROLLER-BALL ULTRASONIC IMAGING MODULE

BACKGROUND OF THE INVENTION

1. Field of the Invention

This invention in general relates to the field of ultrasonic imaging, and more particularly concerns an improved ultrasonic imaging module that effectively eliminates the sliding friction and gouging of the surface of the object to be scanned, such as a patient's skin, and automatically dispenses the proper amount of acoustic coupling fluid as the module moves along the object to be scanned.

2. Description of the Prior Art

In recent years ultrasonic imaging has become important in many areas of medical diagnosis, as for example in obstetrics, cardiology, and in the detection of tumors. Generally, in the ultrasonic imaging process, an ultrasonic camera or, what we shall refer to herein as an ultrasonic imaging module, is placed against and/or moved over the surface of the patient's body, or other object the interior of which it is desired to image. U.S. Pat. No. 4,246,791 describes an example of such a module. Generally, in the trade the term "transducer" is ambiguously applied to the entire ultrasonic "camera" or imaging module, to the piezoelectric element in which electrical energy is transformed into vibrating energy, and also to various portions of the system depending on the viewpoint. For clarity, in this disclosure, we shall refer to the ultrasonic "camera" as an ultrasonic imaging module and shall use the term "transducer" to designate that portion of the camera that actually vibrates. The piezoelectric element in which energy is transformed from electrical to vibrational shall be referred to as the "transducer element." Of course, in some instances, the transducer and the transducer element may be one and the same.

In order to obtain a meaningful ultrasonic image it is necessary that the interface between the ultrasonic imaging dule and the patient be predictable, repeatable, and conductive to the transmission of the ultrasonic energy with minimal distortion. In practice, the presence of some form of coupling fluid between the ultrasonic transducer and the biological tissue of the patient is required to eliminate the existence of a film or gap of air between the transducer and the tissue. Even a thin film of air can be highly detrimental to the effective process of coupling generated ultrasonic energy from the transducer to the patient and, subsequently, coupling the reflected ultrasonic energy, or echoes, from the patient to the transducer. Generally, an acoustic coupling fluid such as Aquasonic Scan TM by Parker Labs, Orange, NJ 07050 is applied to the surface of the patient's body to provide the desired interface. In some applications water provides an adequate coupling agent. Even with the fluid applied to the surface of the patient's body, however, the skin tends to alternately gather, slip irregularly past the transducer, and create other instabilities in the module/patient interface, since it is necessary to press relatively hard on the module against the patient's skin in order to obtain an effective transfer of the ultrasonic energy. Further application of the acoustic coupling fluid is generally done by hand, which results in varying amounts of the fluid being applied and which is also messy and time-consuming. Therefore, it will be highly desirable to provide an ultrasonic imaging module that overcomes these problems.

SUMMARY OF THE INVENTION

It is an object of the invention to provide an ultrasonic imaging module that is characterized by improved ultrasonic coupling at the module/body interface.

It is a further object of the invention to provide an ultrasonic imaging module which provides the above object and, at the same time, rolls easily over the surface of the body in which it is desired to image objects.

It is a further object of the invention to provide an ultrasonic imaging module which automatically applies the proper amount of acoustic coupling fluid to the surface of the body as it passes over it.

In addition, it an object of the invention to provide an ultrasonic imaging module which provides one or more of the above objects and at the same time overcomes one or more of the disadvantages of prior art imaging modules.

The invention provides an ultrasonic imaging module of the type having a transducer for converting electrical energy to a beam of ultrasonic energy and for converting received ultrasonic energy to electrical signals and a means for applying electrical energy to the transducer, the transducer being supported in a housing, which module is characterized by the housing having a bearing for supporting at least a portion of the transducer and the transducer including a sphere rotatably mounted in the bearing. Preferably the transducer includes a transducer element and an ultrasonic window in said housing, said transducer being enclosed in said housing and aligned with said window so the beam of ultrasonic energy passes through the window, and the window comprises the sphere. Preferably, the invention also includes a means for compensating for the effect of the spherical roller-ball on the ultrasonic beam, such as a concave ultrasonic lens located between the transducer element and the window. Preferably, the housing includes an interior chamber which contains the transducer element, and the window forms at least a portion of one wall of the chamber. Preferably, there is also a means for filling the chamber with acoustic coupling fluid under pressure, and the diameter of the spherical window is sufficiently smaller than the diameter of the bearing to permit a film of fluid to pass between the spherical window and the bearing as the window turns in the bearing while being passed over the surface of a body.

Numerous other features, objects and advantages of the invention will become apparent from the following detailed description when read in conjunction with the accompanying drawings.

BRIEF DESCRIPTION OF THE DRAWINGS

In the drawing:

FIG. 1 shows a perspective view of the exterior of an ultrasonic imaging module according to the invention and including a fluid reservoir;

FIG. 2 shows a cutaway side view of the ultrasonic imaging device of FIG. 1, the device applied to the surface of a body;

FIG. 3 shows a cutaway side view of a portion of an alternative embodiment of the invention.

DESCRIPTION OF THE PREFERRED EMBODIMENT

An ultrasonic imaging module 10, according to the invention, as shown in FIG. 1. In use, the end 11 of the module is placed against the surface of the object to be ultrasonically scanned, which for the purposes of this disclosure shall be the skin 14 of a patient. As can be seen in FIG. 2, when the end 11 of the module 10 is placed against the skin 14 of the patient, roller-ball 12 makes contact with skin 14. As roller-ball 12 rolls against the surface of skin 14, a fluid flows from fluid reservoir 15 through hose 16, through the interior 27 of housing 17 and clings to the surface of roller-ball 12 while passing through small channel 18 in the forward end 11 of module 10 and thence is transferred to the surface of skin 14 by roller-ball 12. Wires 19 connect module 10 to electronic circuitry for ultrasonic imaging (not shown).

Turning now to a more detailed description of the structure of the invention. FIG. 2 shows a cutaway side view of ultrasonic imaging module 10, disclosing the interior of the housing 17. As can be recognized by FIGS. 1 and 2, housing 17 is a form of a closed cylinder. At one end 11, walls 21A and 21B are enlarged to form a flange having a bearing surface 22 which defines a portion of the surface of a sphere. Roller-ball 12, shaped in the form of a sphere is mounted in bearing 22; the diameter of roller-ball 12 is slightly smaller than the diameter of bearing surface 22 so that it is free to rotate in the bearing and so that a film of fluid attached to the surface of roller-ball 12 may pass through channel 18 between the surface of bearing 22 and the surface of roller-ball 12. Preferably these diameters are such that channel 18 has a width of approximately 0.005 to 0.030 inches; the optimum diameter of the channel will depend upon the viscosity of the fluid and the pressure in the fluid reservoir 15, which will vary, as known in the art, depending upon the characteristics of the ultrasonic scanning to be performed.

Ultrasonic transducer element 30 is mounted within chamber 27 forming the interior of housing 17. Transducer element 30 is mounted on the end of hollow cylindrical support rod 23 which is, in turn, supported along the axis of chamber 27 by washer-shaped bracket 33. Bracket 33 has holes such as 34 and 35 through it, which permit acoustic coupling fluid to flow freely within the interior of chamber 27. Wires 19 pass through support rod 32 and attach to transducer element 30 to provide the electrical connection between transducer element 30 and the electronic circuitry for driving transducer element 30 and for amplifying and processing the electronic pulses produced by transducer element 30 when ultrasonic energy impinges upon it. In the embodiment shown, ultrasonic lens 36 is bonded to transducer element 30, although in other embodiments it may be supported by its own bracket within chamber 27. Inlet port 25, which is a short hollow cylinder formed in the surface of housing 17 communicates with opening 26 in housing 17. Hose 16 has an internal diameter such that it fits tightly about the cylinder 25; a clamp may be used to hold tube 16 on cylinder 25, if desirable.

Hose 16 connects chamber 27 with a fluid reservoir 15, which may be any conventional source of pressurized fluid, such an aerosol pressurized container, a compressible bladder filled with fluid, a pump or, in one embodiment, even a conventional water faucet. In the preferred embodiment a reservoir pressurized by gas (aerosol) is used since it is convenient and since it has no source of noise connected to it.

An alternative embodiment of a module 50, according to the invention, is shown in FIG. 3. In this embodiment, housing 51, roller-ball 52, and bearing 53 are as described above. The difference in this embodiment is that transducer element 58 is a hemispherical transducer element, which compensates for the spherical shape of roller-ball window 52 without the need for a lens such as 36. That is, a suitably small hemispherical transducer element will radiate sound in a divergent pattern which will be focused by roller-ball 52 so that ultrasonic radiation emerges in a more parallel or convergent beam (as opposed to a divergent beam) from the surface of roller-ball 52, as shown by the dotted lines 61 and 62. Transducer element 58 is mounted on rod 59 and connected to the electronics as previously discussed in relation to FIG. 2.

Roller-ball window 12 and 52 and lens 36 are preferably made of acrylate plastic, or any other suitable plastic or other material conventionally known as suitable for focusing of ultrasonic beams. Transducer elements 30 and 58 may be made of barium titanate or any other suitable ultrasonic transducer element material as conventionally known in the art. Housing 17, including port 25 and flanges 21a and 21b as well as bracket 33 may be made of ABS plastic or any other suitable plastic or other metal or other material, preferably one that is injection-moldable. Rod 32 may also be formed of ABS plastic, or Teflon ®, or brass or any other suitable plastic or metal. Tubing 16 may be made of silicone rubber, polyurethane, or any other synthetic or natural rubber composite or other pliable material.

In the above embodiments it should be clear that the "transducer" as defined in the Background of the Invention above, includes the transducer element 30, the lens 36 and the roller-ball 12 in the embodiment of FIG. 2 and the transducer element 58 and roller-ball 52 in the embodiment of FIG. 3. In other embodiments, the transducer may consist of the roller-ball alone, in which case the roller-ball would be made of barium titanate or any other suitable piezoelectric materials.

A feature of the invention is that the roller-ball such as 12, provides a predictable and constant interface for application of ultrasonic sound to the surface of skin 14. The ball rolls smoothly over the surface of skin 14 and skin 14 does not tend to gather and ripple as the ball, such as 12, is moved. Rather, as the ball moves over the surface of the skin the ball/skin interface tends to remain constant. Moreover, the ball applies a film of coupling fluid of constant thickness to the surface of skin 14 which not only further lubricates the flow of the ball over the skin 14, but also provides a predictable and constant coupling medium.

There has been described a novel ultrasonic imaging module that provides for greatly improved coupling between the module and the object to be imaged. While the invention has been described in connection with several particular embodiments, one skilled in the art will appreciate that numerous other embodiments and departures from the embodiments shown may be made without departing from the inventive concepts. For example, lens 36 or element 58 may be a combination of various lens or elements and lens to achieve the desired shaping or focusing of the ultrasonic beam. A means for compensating for the effect of the roller-ball on the ultrasonic beam may be contained in the ultrasonic electronics rather than a means affecting the ultrasonic beam itself. As a further example, more with a single roller-ball window 12. A wide variety of dimensions, shapes and materials for transducers, windows, and other elements may be chosen by those skilled in the art to arrive at the desired characteristics as described. Clearly the invention contemplates the possibility of a plurality of the roller-ball transducer being used together. In addition, other features may be added while still employing the inventive concepts. It is therefore to be understood that, within the scope of the appended claims, the invention may be practiced other than as it has been specifically described.

What is claimed is:

1. An ultrasonic imaging module of the type having a transducer for converting electrical energy to a beam of ultrasonic energy and for converting received ultrasonic energy to electrical signals and a means for applying electrical energy to said transducer, the transducer being supported in a housing the imaging module characterized by:

the transducer including a transducer element mounted in the housing;

said housing including a bearing;

said housing including a chamber for holding fluid;

said transducer including a spherical ultrasonic widow rotatably mounted in said bearing and aligned with the transducer element; and a source of fluid under pressure with a fluid conduit connecting said source to the chamber for maintaining fluid in said housing, whereby fluid is applied to a surface to which ultrasonic energy is coupled, through contact of the spherical ultrasonic window with said surface.

2. An ultrasonic imaging module as in claim 1 wherein said ultrasonic transducer element is mounted in said chamber, and further comprising a concave ultrasonic lens located in said chamber between said transducer and said window.

3. An ultrasonic imaging module as in claim 1 and further including a fluid filling said chamber.

4. The ultrasonic imaging module of claim 1 further comprising:

means for compensating for the effect of said spherical ultrasonic window and said ultrasonic beam.

5. An ultrasonic imaging module as in claim 4 wherein said means for compensating comprises a concave ultrasonic lens located between said transducer element and said window.

* * * * *